United States Patent [19]

Chen et al.

[11] Patent Number: 5,192,498
[45] Date of Patent: Mar. 9, 1993

[54] ELIMINATION OF SULFIDE ODOR IN THIOCARBAMATE HERBICIDES

[75] Inventors: Chia-Chung Chen, Tsaoton, Taiwan; Ray J. Lo, Alameda, Calif.

[73] Assignee: Imperial Chemical Industries plc, London, Great Britain

[21] Appl. No.: 775,680

[22] Filed: Oct. 11, 1991

[51] Int. Cl.$^5$ .................. A61L 2/00; A01N 37/00
[52] U.S. Cl. ..................... 422/5; 71/DIG. 1; 504/300; 504/305; 504/220; 504/249; 504/287
[58] Field of Search ............... 422/5; 71/100, DIG. 1

[56] References Cited

U.S. PATENT DOCUMENTS

| | | | |
|---|---|---|---|
| 4,125,589 | 11/1978 | deVries | 422/5 X |
| 4,541,986 | 9/1985 | Schwab et al. | 422/5 |
| 4,594,239 | 6/1986 | Pluim, Jr. | 422/5 X |
| 4,803,047 | 2/1989 | Pluim, Jr. | 422/5 |
| 5,019,339 | 5/1991 | Keeney et al. | 422/5 X |

*Primary Examiner*—Robert J. Warden
*Assistant Examiner*—Stephanie Blythe
*Attorney, Agent, or Firm*—William E. Dickheiser

[57] ABSTRACT

It has now been discovered that the undesirable odor in thiocarbamate compounds can be suppressed or mostly eliminated by the process of this invention. Generally, the process of this invention involves mixing an aqueous solution of sodium hypochlorite, calcium hypochlorite or chloramine-B with the odorous thiocarbamate compound for a sufficient period of time, followed by a second step of mixing citric acid, maleic acid or oxalic acid with the treated thiocarbamate compound to eliminate chlorodialkylamine compounds produced in the first step.

7 Claims, No Drawings

ELIMINATION OF SULFIDE ODOR IN THIOCARBAMATE HERBICIDES

This invention relates to a process for the elimination of sulfide odor in thiocarbamate herbicides and, in particular, to a process for the elimination of disulfide odor.

BACKGROUND OF THE INVENTION

Thiocarbamate herbicidal compounds have been commercially sold since the 1950,s and are very effective in controlling weeds in a variety of crops such as rice, potatoes, sugarbeets, sunflowers and tobacco. These herbicidal compounds have been described in a variety of patents such as U.S. Pat. Nos. 2,913,317, 2,919,182, 3,037,853, 3,175,897, 3,185,720, 3,198,786 and 3,582,314.

Preferred thiocarbamate compounds of this invention have the following structural formula:

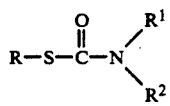

wherein
R is ethyl, n-propyl, isopropyl, 2,3-dichloroallyl, 2,3,3-trichloroallyl, benzyl or p-chlorobenzyl, preferably ethyl, n-propyl or isopropyl;
$R^1$ is $C_1$–$C_6$ alkyl, preferably $C_2$–$C_4$ alkyl; and
$R^2$ is $C_2$–$C_6$ alkyl, preferably ethyl, propyl, isopropyl, n-butyl, isobutyl, dimethylpropyl and cyclohexyl; or
$R^1$ and $R_2$ together are a $C_3$–$C_6$ alkylene group optionally substituted with methyl, preferably pentylene.

Thiocarbamate compounds that have been sold commercially since 1958 are as follows:

| Chemical Name | Common Name |
| --- | --- |
| S-ethyl dipropyl thiocarbamate | EPTC |
| S-ethyl diisobutyl thiocarbamate | butylate |
| S-ethyl N-cyclohexyl-N-ethyl thiocarbamate | cycloate |
| S-ethyl hexahydro-1H-azepine-1-carbothioate | molinate |
| S-propyl dipropyl thiocarbamate | vernolate |
| S-propyl butylethyl thiocarbamate | pebulate |
| S-2,3,3-trichloroallyl diisopropyl thiocarbamate | triallate |
| S-2,3-dichloroallyl diisopropyl thiocarbamate | diallate |
| S-p-chlorobenzyl diethyl thiocarbamate | thiobencarb |
| Ethyl-1-hexahydro-1,4-azepine-1-carbothioate | byram |
| S-benzyl N,N-di-sec.-butyl thiocarbamate | tiocarbazil |
| S-benzyl N-ethyl-N-2,3-dimethylpropyl thiocarbamate | esprocarb |

Commercially, most thiocarbamate compounds are prepared by first reacting appropriately substituted mercaptan (ethyl mercaptan) with phosgene to give a carbamoyl chloride. Next, the substituted chlorothio formate (ethyl chlorothioformate) is reacted with an appropriately disubstituted amine (di-n-propylamine) to give the desired thiocarbamate compound (S-ethyl di-n-propyl thiocarbamate).

During the manufacture of technical thiocarbamate compounds, several odorous compounds are formed that contaminate the final product. Also, these odorous compounds sometimes are present in starting materials such as the substituted mercaptans and they are carried through the manufacturing process steps to the final thiocarbamate product. Additionally, upon storage of thiocarbamate compounds, they tend to slightly degrade or decompose to produce odorous compounds.

These odorous compounds are believed to have the structural formulae:

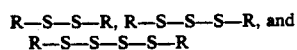

wherein R is as defined above, and will depend upon the particular thiocarbamate compound that is being manufactured. Especially odorous compounds are believed to have the structural formula

wherein R is ethyl, n-propyl, benzyl, p-chlorobenzyl, 2,3-dichloroallyl or 2,3,3-trichloroallyl.

One of the most odorous compounds is believed to be diethyl disulfide (DDS).

SUMMARY OF THE INVENTION

It has now been discovered that the most undesirable odor in thiocarbamate compounds can be suppressed or mostly eliminated by the process of this invention. Generally, the process of this invention involves a first step of mixing an aqueous solution of sodium hypophlorite, calcium hypochlorite, chloramine-B hydrate or chloramine-T hydrate with the odorous thiocarbamate compound for a sufficient period of time, followed by a last step of mixing citric acid, maleic acid or oxalic acid with the treated thiocarbamate compound to eliminate any chlorodialkylamine compounds produced during the first step.

DETAILED DESCRIPTION OF THE INVENTION

The first step of this invention involves mixing an aqueous solution of sodium hypochlorite, calcium hypochlorite, chloramine-B hydrate or chloramine-T hydrate with technical thiocarbamate compound as defined above. An aqueous solution of sodium hypochlorite is preferred.

Preferably, from about 1 to about 10 parts by weight per 100 parts by weight thiocarbamate of the sodium hypochlorite, calcium hypochlorite, chloramine-B hydrate or chloramine-T hydrate should be mixed with the technical thiocarbamate. More preferably, above 1 to about 7 parts by weight should be added.

The concentration of the above-described sodium hypochlorite, calcium hypochlorite, chloramine-B hydrate or chloramine-T hydrate in an aqueous solution is not critical and preferably can vary from about 1 percent to about 75 percent by weight of water, preferably from about 5 to about 7 percent by weight.

The technical thiocarbamate compound to be deodorized and the aqueous solution can be mixed in any convenient vessel. Preferably, the mixing is done at room temperature, although lower or higher temperatures can be used.

Generally, mixing time is dependent on the type of mixing and the amount of contaminating odor-causing compound in the technical thiocarbamate. Mixing times of about 30 minutes have been found effective for a 5% aqueous solution of sodium hypochlorite. Longer mixing times of about 2 hours are necessary for 5% aqueous solutions of calcium hypochlorite, chloramine-B hydrate or chloramine-T hydrate.

After the mixing step is discontinued, the treated technical thiocarbamate can be separated from an aqueous bottom layer by simple phase-separation techniques. The aqueous layer will contain any unreacted sodium hypochlorite, calcium hypochlorite, chloramine-B hydrate or chloramine-T hydrate.

Preferably, the separated, treated technical thiocarbamate compound is given one or more water washes to remove any residual sodium hypochlorite, calcium hypochlorite, chloramine-B hydrate or chloramine-T hydrate.

During the first mixing step, the aqueous solution of sodium hypochlorite, calcium hypochlorite, chloramine-B hydrate or chloramine-T hydrate reacts with a small amount of the thiocarbamate being treated to form an amine having the structural formula

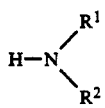

which is chlorinated to form a compound having the structural formula

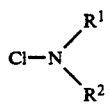

where $R^1$ and $R^2$ are described as above.

The chloroamine compound is toxic and is very undesirable in the final technical thiocarbamate compound.

The chloroamine compound can be removed by reacting it with either oxalic acid, maleic acid or citric acid without compound.

Generally, about 0.01 to about 0.5 parts by weight the acid should be mixed with the treated thiocarbamate compound of the first step to react with any chloroamine compound that formed during the first step. Extra acid can be added without harmful effects, but the extra amounts are not necessary.

Preferably, about 0.1 to about 0.5 parts by weight acid should be added. Excess unreacted acid need not be removed from the final technical thiocarbamate.

The technical thiocarbamate product of the process of this invention can be formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds can be formulated as granules of relatively large particle size, as wettable powders, as emulsifiable concentrates, as powdery dusts, as flowables, as solutions or as any of several other known types of formulations, depending upon the desired mode of application. These formulations may contain as little as about 0.5% to as much as about 95% or more by weight of active ingredient.

EXAMPLE 1

This example shows the calibration of diethyldisulfide (DDS) standards in the headspace of a gas chromatograph versus a known added amount of DDS in a sample of pure EPTC in the liquid phase.

Samples were prepared by adding the indicated micrograms of DDS to a gram of pure EPTC. The headspace area count for the DDS was taken with a Perkin-Elmer Model HS-100 Automatic Headspace Analyzer coupled with a Perkin-Elmer Sigma-2000, gas chromatograph (GC) equipped with a Flame Ionization Detector.

The experimental procedure was as follows:

Samples were placed in Headspace GC containers and volatile components were quantified according to the following procedure:

| Capillary Gas Chromatography Conditions | |
|---|---|
| Column: | 30 m × 0.25 mm id, 1.0 micron film thickness, DB-1, fused silica capillary column. |
| Temperatures: (Oven) | 40° C. for 3 minutes, then 10° C. per minute to 210° C. for 5 minutes Detector Temp: 260° C. |
| Flow Rates: | Carrier Gas (Helium): 30 cm/sec at 100° C. |
| | Make-up Gas (Helium): 30 mL/min |
| | Hydrogen: 30 mL/min |
| | Air: 400 mL/min |
| Elution Order: | DDS 8.4 minutes |
| | Standard 8.4 minutes |
| Headspace Autosampler Conditions | |
| Sample Temperature: | 40° C. |
| Transfer Temperature: | 70° C. |
| Thermostatting Time: | 120 min. |
| Pressurization Time: | 0.5 min. |
| Injection Time: | 0.08 min. |
| Withdrawal Time: | 0.2 min |
| Cycle Time: | 40.0 min |

| Sample No. | Added DDS μg/g or P.P.M. | DDS Headspace Area Count |
|---|---|---|
| 1. | 0 | 2,620 |
| 2. | 12.6 | 5,226 |
| 3. | 25.8 | 8,089 |
| 4. | 97.4 | 25,150 |
| 5. | 266 | 56,061 |
| 6. | 1,100 | 239,695 |
| 7. | 4,680 | 1,178,556 |
| 8. | 9,380 | 2,348,219 |

EXAMPLE 2

This example shows the reduction of DDS in a sample of commercially manufactured technical EPTC by mixing therein of certain chemical reagents.

The analysis was run by adding 10 milliliters (ml) of newly manufactured technical EPTC to a 50 ml widemouth, clear glass bottle. This untreated sample was stirred with a magnetic stirrer for 4 hours at room temperature. The sample had a strong mercaptan odor. The sample was analyzed for diethyldisulfide by doing a gas chromatograph area count according to the procedure of Example 1. The untreated sample had an area count of 325,000 which calculates, according to the data relationship of Example 1, to be about 1,300 p.p.m.

Next, the above experiment was repeated with the exception that 5 parts by weight of the listed chemical samples were analyzed for DDS by determining the gas chromatograph area count using the same procedure as described in Example 1.

The results are reported in Table 1.

TABLE 1

| Chemical Reagent | DDS Headspace Area Count |
|---|---|
| None | 325,000 |
| Toluenesulfonyl chloride | 266,000 |

TABLE 1-continued

| Chemical Reagent | DDS Headspace Area Count |
| --- | --- |
| $KIO_3$ | 275,000 |
| $KIO_4$ | 270,000 |
| $K_2CrO_4$ | 276,000 |
| $K_2Cr_2O_7$ | 279,000 |
| $KMnO_4$ | 267,000 |
| $I_2$ | 293,000 |
| $H_2O_2$/Acetic Acid | 188,000 |
| $CrO_3$ | 126,000 |
| Chloramine-B Hydrate[a] | 69,000 |
| $Ca(OCl)_2$ | 38,000 |
| NaOCl | 4,000 |

[a] N-chlorobenzenesulfonamide, sodium salt
$C_6H_5SO_2N(Cl).XH_2O$ FW 213.62, m.p. 170–173° C.

EXAMPLE 3

This example shows the chemical stability of technical EPTC after mixing with an aqueous solution of sodium hypochlorite.

The untreated EPTC technical sample from Example 2 was analyzed by gas chromatographic techniques using a Hewlett-Packard Model 5890 gas chromatograph by the following procedure.

Weight Percent Active Ingredient Analysis of EPTC Technical by Capillary Gas Chromatorgraphy An EPTC sample was dissolved in methyl benzoate which contained a known amount of another thiocarbamate (molinate) as the internal standard. The solution was analyzed by a Hewlett-Packard Model 5890 gas chromatograph equipped with a flame ionization detector.

Internal Standard Preparation

A solution containing 100 mg molinate per 20 mL methyl benzoate was prepared.

Calibration Solution Preparation

Weigh 100 mg EPTC reference standard into a 1 oz bottle and add, via volumetric pipet, 20 mL of the molinate internal standard solution. Cap the bottle and shake to mix.

Technical EPTAM Sample Solution Preparation

Weight 100 mg of the technical EPTAM sample into a 1 oz bottle and add, via volumetric pipet, 20 mL of the molinate internal standard solution. Cap the bottle and shake to mix.

| Capillary Gas Chromatography Conditions | |
| --- | --- |
| Column: | 15 m × 0.25 mm id, 0.25 micron film thickness, DB-210, fused silica capillary column. |
| Temperatures: (Oven) | 100° C. for 4 minutes, then 10° C. per minute to 140° C. for 1 minute Injector Temp: 200° C. Detector Temp: 250° C. |
| Flow Rates: | Carrier Gas (Helium): 30 cm/sec at 150° C. Make-up Gas (Helium): 30 mL/min Hydrogen: 30 mL/min Air: 400 mL/min |
| Elution Order: | EPTC 1.41 minutes molinate 2.41 minutes |
| Injection Volume: | 2 μL |
| Split Ratio: | 125:1 |

The weight percent of EPTC was determined by comparing its chromatographic response to the internal standard, molinate, in the sample and calibration solutions.

The untreated sample of EPTC technical was found to contain 98.4% by weight S-ethyl dipropyl thiocarbamate.

The NaClO treated EPTC sample of Example 2 was found to initially contain 97.0% by weight S-ethyl dipropyl thiocarbamate. Aging of the sample for 4 weeks at −10° C. and 50° C. caused no loss of S-ethyl dipropyl thiocarbamate. Analysis was 97.0 and 97.4% by weight, respectively, for the aged samples.

EXAMPLE 4

This example shows the effectiveness of several acids to remove N-chlorodipropylamine (CDA) from samples of sodium hypochlorite treated EPTC technical compounds.

Both the untreated and the chemical reagent-treated samples of technical EPTC from Example 2 were analyzed by gas chromatographic techniques according to the procedure of Example 1.

The analytical results indicated the presence of CDA in the samples treated with the chemical reagents, chloramine-B hydrate, $Ca(OCl)_2$ and NaOCl. CDA is believed to be formed by the hydrolysis of EPTC (S-ethyl dipropylthiocarbamate) and the chemical reagents of Example 2 to form dipropylamine which reacts with the chemical reagents chloramine-B hydrate, $Ca(OCl)_2$ or NaOCl to form N-chlorodipropylamine (CDA).

The experimental procedure was as follows:

A 10 gram sample of the sodium hypochlorite (NaOCl) treated EPTC sample of Example 2, and a 10 gram sample of the untreated EPTC sample of Example 2 were placed in 50 ml clear glass bottles having a magnetic stirrer. Next, 10 ml of 1N hydrochloric acid or 0.1 grams of several solid organic acids listed in Table 2 were added to samples of the NaOCl treated EPTC. The samples were stirred for 16 hours at room temperature. The organic and aqueous HCl layers were separated with a separatory funnel. However, the EPTC samples treated with solid organic acids did not require any separation procedure. The EPTC technical sample, EPTC technical treated with NaOCl from Example 2, and the various acid addition samples of the EPTC technical treated with the NaOCl were submitted for headspace gas chromatograph analysis. The DDS analysis was run according to the procedure outlined in Example 2. The CDA analysis was run in a similar manner to the head count analysis of the DDS in Examples 1 and 2.

The results are listed in Table 2.

TABLE 2

Amount of CDA in Samples of EPTC Technical[a]
Addition of 0.1% by Weight of Various Acids

| | Area Counts in Headspace | |
| --- | --- | --- |
| Acid Addition | CDA | DDS |
| None - Untreated EPTC technical | 0 | 1,392,000 |
| None - NaClO-treated EPTC technical | 886,000 | 7,000 |
| 1 N HCl | 0 | 224,000 |
| Ethylenediaminetetracetic acid | 1,946,000 | 4,000 |
| Lauric acid | 1,464,000 | 3,000 |
| Acetic acid | 320,000 | 4,000 |
| Benzoic acid | 350,000 | 4,000 |
| Oxalic acid | 0 | 80,000 |
| Maleic acid | 0 | 10,000 |
| Citric acid | 0 | 4,000 |

TABLE 2-continued

Amount of CDA in Samples of EPTC Technical[a]
Addition of 0.1% by Weight of Various Acids

| Acid Addition | Area Counts in Headspace | |
|---|---|---|
| | CDA | DDS |
| None - EPTC (pure) | 0 | 1,000 |

[a]Sample from Example 1

The results of Table 2 show that oxalic, maleic and citric acids are very effective acid additives to reduce CDA without significantly increasing the amount of DDS in the samples of technical EPTC previously treated with sodium hypochlorite.

EXAMPLE 5

The procedure of Example 2 was repeated except that cycloate was substituted for EPTC. The DDS headspace area count for cycloate having no chemical reagent added was 189,549. When 5 parts by weight of sodium hypochlorite per 100 parts by weight cycloate was mixed into the cycloate for 30 minutes at room temperature, the DDS headspace area count was found to be reduced to a non-detectable amount.

The foregoing descriptions are offered primarily for purposes of illustration. It will be readily apparent to those skilled in the art that additional structures as well as modifications and substitutions in the materials, system parameters, and procedures herein described may be made without departing from the spirit and scope of the invention.

What is claimed is:

1. A process for reducing mercaptan odor from a thiocarbamate compound comprising the steps of:
   A) mixing an aqueous solution containing from about 1 to about 10 parts by weight of sodium hypochlorite, calcium hypochlorite, chloramine-B hydrate or chloramine-T-hydrate with 100 parts by weight of thiocarbamate to form treated thiocarbamate and an aqueous layer;
   B) separating the aqueous layer from the treated thiocarbamate; and
   C) mixing from about 0.01 to about 0.5 parts by weight of oxalic acid, maleic acid or citric acid with 100 parts by weight of the treated thiocarbamate.

2. The process of claim 1 where the thiocarbamate compound has the structural formula

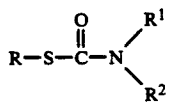

wherein
R is ethyl, n-propyl, isopropyl, 2,3- dichloroallyl, 2,3,3- trichloroallyl, benzyl or p-chlorobenzyl;
$R^1$ is $C_1$-$C_6$ alkyl; and
$R^2$ is $C_2$-$C_6$ alkyl or cyclohexyl.

3. The process of claim 2 wherein from about 1 to about 10 parts by weight of sodium hypochlorite are mixed with the thiocarbamate.

4. The process of claim 2 wherein from about 1 to about 5 parts by weight of sodium hypochlorite are mixed with the thiocarbamate compound and about 0.1 to about 0.5 parts citric acid are added to the treated thiocarbamate after the separating step.

5. The process of claim 4 where the concentration of the sodium hypochlorite in the aqueous solution is about 5 to about 7 percent by weight.

6. The process of claim 5 wherein the thiocarbamate is S-ethyl dipropyl thiocarbamate.

7. The process of claim 6 wherein the thiocarbamate is S-ethyl hexanhydro-1H-azepine-1-carbothioate.

* * * * *